Figure 1:
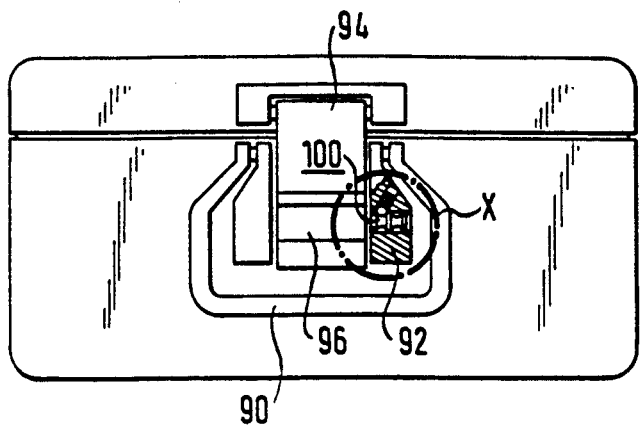

United States Patent [19]

Wagner

[11] Patent Number: 5,147,351

[45] Date of Patent: Sep. 15, 1992

[54] SAFETY SEAL FOR STERILIZABLE CONTAINERS

[75] Inventor: Peter Wagner, Starnberg-Söcking, Fed. Rep. of Germany

[73] Assignee: Wagner GmbH, Fed. Rep. of Germany

[21] Appl. No.: 743,138

[22] Filed: Aug. 9, 1991

[30] Foreign Application Priority Data

Aug. 10, 1990 [EP] European Pat. Off. ........ 90115428.6

[51] Int. Cl.$^5$ .............................................. E05C 1/02
[52] U.S. Cl. ............................ 292/284; 292/DIG. 66; 292/144
[58] Field of Search ................ 116/221, 216; 292/144, 292/147, 164, 283, 284, DIG. 66, 252

[56] References Cited

U.S. PATENT DOCUMENTS

| | | | |
|---|---|---|---|
| 1,800,818 | 4/1931 | Devereaux | 292/352 X |
| 3,807,779 | 4/1974 | Enders | 292/147 |
| 4,539,929 | 9/1985 | Sestak et al. | 292/DIG. 66 |
| 4,753,465 | 6/1988 | Dalby | 292/DIG. 66 X |
| 5,050,778 | 9/1991 | Carrado et al. | 292/144 |

FOREIGN PATENT DOCUMENTS

| | | |
|---|---|---|
| 3710049 | 10/1988 | Fed. Rep. of Germany . |
| 3632674 | 1/1989 | Fed. Rep. of Germany . |
| 2335239 | 7/1977 | France . |
| 7900077 | 2/1979 | World Int. Prop. O. . |
| 8102108 | 8/1981 | World Int. Prop. O. . |
| 8707151 | 12/1987 | World Int. Prop. O. . |

Primary Examiner—Richard E. Moore
Attorney, Agent, or Firm—Ostrolenk, Faber, Gerb & Soffen

[57] ABSTRACT

A safety seal for sterilizable containers that is closed by the temperature prevailing in the sterilizer. The closed seal then indicates the integrity of the container. The sealing mechanism in the illustrated embodiment is a pushbutton 100 that is subject to the force of a spring 102. The spring is made of a memory-retaining alloy that provides tension at a temperature above a transition temperature and forces the pushbutton into a locking state. The container can be opened once the pushbutton has been forced back, but the pushbutton cannot be returned to its locking position until it attains the transition temperature again.

3 Claims, 2 Drawing Sheets excludes a memory-retaining metal alloy. Capsule 202 is accommodated in bore 98 with a compression spring 204 between them. Spring 204 holds the capsule against cap 116. Spring 204 is weaker than the capsule when the latter is exposed to sterilization temperature.

SAFETY SEAL FOR STERILIZABLE CONTAINERS

Sterilizable containers, which accommodate surgical instruments and other sterile materials during and after sterilization, are secured closed with a seal. An undamaged seal indicates that the container's lid has not been removed since sterilization of the vessel's contents. It can accordingly be concluded that the contents are uncontaminated by germs.

Conventional seals comprise plastic rings that applied to the joint between the container and its lid such that the apparatus cannot be opened without irreparably destroying the ring. Such rings are expensive because they can only be used once.

Also applied to sterilizable containers are devices that by responding to the heat of sterilization (or to a prescribed difference in pressures) indicate that the apparatus has undergone a sterilization sequence.

With a safety seal of the genus recited in the preamble to claim 1 as a point of departure, the object of the present invention is to improve it to the extent that it can be reused and will as well indicate that sterilization has occurred.

This object is attained by the characteristics recited in the body of claim 1.

One preferred embodiment of the invention employs an alloy that incorporates a memory function, transforming from a martensitic to an austenitic structure once a specific temperature has been attained. A spring made of such an alloy will have a very low characteristic if any below that transition temperature and a high characteristic above it. It will tension all at once. A spring is in accordance with the invention made of such a memory-retaining alloy and forces a sealing component closed once the transition temperature has been attained. The sealing component accordingly locks into a state that it can only be extracted from by manual pressure once the temperature has dropped below the transition temperature. The sealing component will then retain the open state that it has been forced into. A sealing component that has been forced into a closure state subject to the tensioned memory-retaining spring will accordingly indicate that sterilization has occurred.

Figure 2:
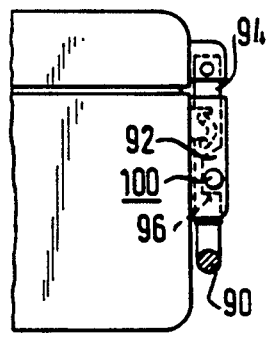
Figure 3:
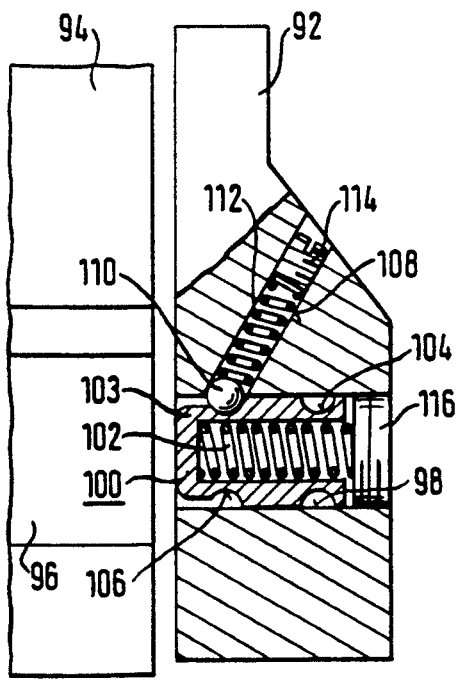
Figure 4:
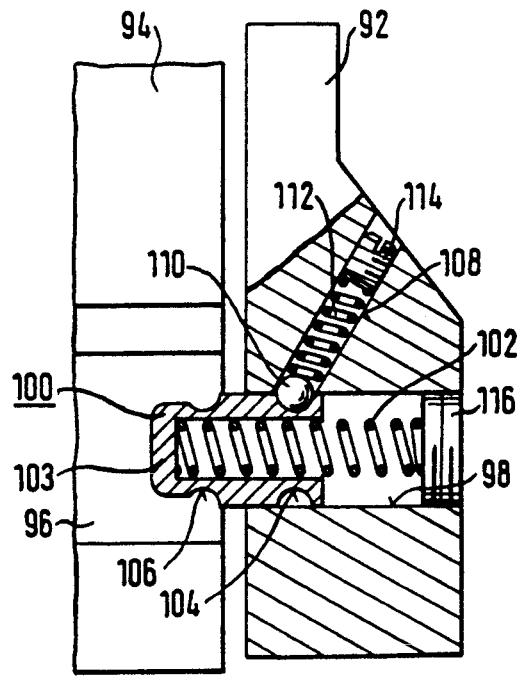

One embodiment of the invention will now be specified with reference to the drawing, wherein FIG. 1 is a front view of a sterilizable container with a metal memory-retaining seal, FIG. 2 is a side view of the container illustrated in FIG. 1, FIG. 3 is a larger-scale view of the area X in FIG. 1, illustrating the seal in the open state, and FIG. 4 is a view of area X at the same scale but illustrating the seal in the closure state.

Figure 5:
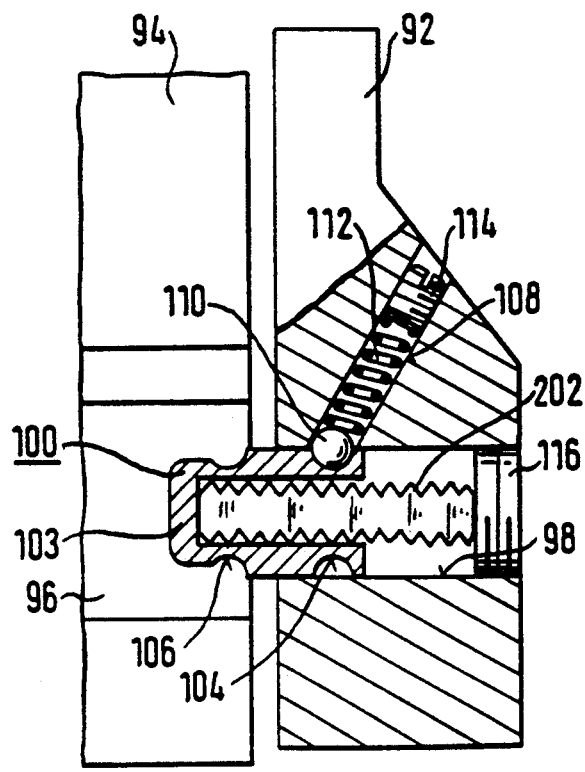
Figure 6:
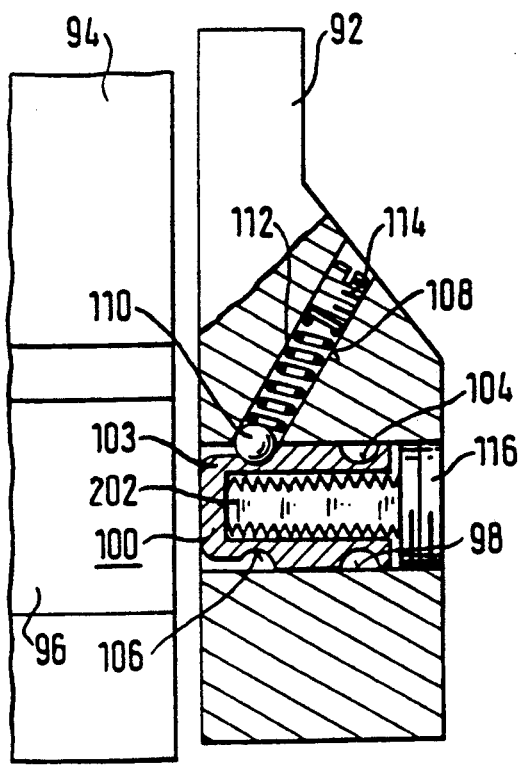

FIGS. 5 and 6 are views corresponding to respective FIGS. 3 and 4 illustrating a second embodiment of this invention.

The sterilizable container illustrated in FIG. 1 has a lock 92. The apparatus' handle 90 pivots on this lock 92. The lock 92 can be secured in a known way with a bracket 94. There is a recess 96 at the bottom of the bracket 94. Lock 92 has a bore 98 extending through it in the vicinity of recess 96. A hollow pushbutton 100 fits into the bore 98. The outside of the bore 98 is closed with a cap 116 that either screws into the bore if it is threaded or is inserted into it and secured with a grub screw (not shown). One end of a helical compression spring 102 rests against cap 116. This spring 102 is accommodated on pushbutton 100 with its other end resting against the base 103 of that structure. Spring 102 is made from a memory-retaining alloy and has practically no characteristic below a prescribed temperature. When heated beyond that temperature, however, the alloy undergoes certain changes that considerably increase the spring's characteristic. Spring 102 will accordingly force pushbutton 100 to the left, out of the position illustrated in FIG. 3 and into the locking position illustrated in FIG. 4, in which it will be in the vicinity of the recess 96 in bracket 94. The bracket cannot now be swung up, and the cover cannot be removed from the container.

The transition temperature can be 65° for example. It may be higher, but not be as high as sterilization temperature.

Pushbutton 100 will inhere in both the unlocking position illustrated in FIG. 3 and the locking position illustrated in FIG. 4. It will accordingly have both a rear groove 104 and a forward groove 106 around it. Lock 92 also has a sloping bore 108 that opens into bore 98 and contains a locking ball 110 that is forced into groove 104 or 106 by a helical compression spring 112. The rear end of spring 112 rests against a setscrew screwed into a threaded section of sloping bore 108. Components similar to those illustrated in FIGS. 1 through 4 are also on the opposite side of the container and for practical purposes on the same side of bracket 94, on the right as illustrated in FIG. 1 for example. This arrangement will prevent the lid being removed from the locked container and will simultaneously allow the pushbutton to be pushed in the same direction with the same finger of the right or left hand from the locking position and into the unlocking position.

The sterilizable container is introduced, with its seal open as illustrated in FIGS. 1 and 3, into the sterilizer. When the memory-retaining metal alloy attains transition temperature, the characteristic of spring 102 will increase considerably, and the spring will force pushbutton 100 to the left, out of the position illustrated in FIG. 3 and into the position illustrated in FIG. 4. Locking ball 110 will be lifted out of forward groove 106 and will drop into its locking position in rear groove 104. Pushbutton 100 will remain in this position once the temperature has dropped below transition temperature, and spring 102 will exert practically no more force. In this position, the pushbutton will, as illustrated in FIG. 4, block and thereby prevent brackets 94 from opening on either side and will indicate that the container has been sterilized and has not been opened since. To open the container, the pushbuttons 100 on each side must be forced manually into bore 98 until locking ball 110 drops back into forward groove 106. It will now become possible to pivot bracket 94 out and remove the lid. Once the pushbutton has been forced into the position illustrated in FIG. 3, it will be impossible to force it into the locking position until it has once more been exposed to the transition temperature.

One embodiment has been hereintofore described to illustrate the essence of the invention. The basic principle of the invention, of locking with a safety seal, can, however, also be otherwise embodied. Thus the temperature-responsive memory-retaining alloy spring 102 can be replaced by a compression capsule 202 (FIGS. 5 and 6) that expands lengthwise during sterilization and forces pushbutton 100 to the left as illustrated in FIG. 3.

More particularly, to construct an apparatus embodying the second embodiment of this invention, spring 102 of the first embodiment (FIGS. 3 and 4) is replaced by capsule 202 (FIGS. 5 and 6) that is filled with air at atmospheric pressure. When the sterilizable container is first placed in a sterilizer (not shown) the elements of the second embodiment are in their positions shown in FIG. 5 with pushbutton 100 withdrawn from recess 96. During sterilization, temperature within the sterilizer rises, air pressure drops and the pressure within capsule drops toward equalization with this reduced pressure or vacuum. In so doing capsule 202 expands lengthwise and thereby forces pushbutton 100 to the left from the open position of FIG. 5 to the blocking position of FIG. 6 wherein pushbutton 100 enters recess 96. Since the ends of capsule 202 are not cemented or otherwise attached to the elements that they bear against in FIG. 6, when capsule 202 contracts during cooling, pushbutton 100 remains in its locking position of FIG. 6, wherein ball 110 is disposed within depression 104, but is free to be moved manually to the right to its retracted position of FIG. 5 wherein ball 110 is disposed within depression 106. With pushbutton 100 retracted it no long blocks operation of bracket 94.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

I claim:

1. Safety seal for sterilizable containers, with a definite closure state that ensures that the container has remained closed subsequent to sterilization and with an open state that indicates that it has been opened subsequent to sterilization, characterized in that the seal has a locking mechanism (100) that automatically mechanically locks the container closed subject to the heat of sterilization, a bracket (94) for maintaining said container closed, the locking mechanism including a pushbutton (100) that inheres in both a locking and an unlocking position (104 & 106) relative to bracket (94) and that can be manually shifted into the unlocking position at will, said pushbutton (100) when in said locking position blocking operation of said bracket (94) and thereby prevent opening of said container, said pushbutton (100) requiring application of direct manual force for operation to said unlocking position clear of said bracket (94) whereby the latter may be operated to permit opening of said container.

2. Safety seal as in claim 1, further characterized by having a spring (102) for forcing the locking mechanism (100) into the closure state, said spring (102) being made of a memory-retaining alloy that does not provide force to move the mechanism (100) into the closure state until spring (102) has exceeded a transition temperature.

3. Safety seal as in claim 1, further characterized by having an expandable capsule (202) for forcing the locking mechanism into the locking position, said capsule (202) expanding when subjected to vacuum that in present during sterilization of the sterilizable container to force the locking mechanism into the locking position to maintain the container closed.

* * * * *